United States Patent [19]

Chaudhuri et al.

[11] Patent Number: 5,110,585

[45] Date of Patent: May 5, 1992

[54] QUATERNIZED NITROGEN CONTAINING POLYCYCLIC COMPOUNDS

[75] Inventors: Ratan K. Chaudhuri, Butler; David J. Tracy, Lincoln Park; Robert B. Login, Oakland; Michael W. Helioff, Westfield, all of N.J.

[73] Assignee: ISP Investments Inc., Wilmington, Del.

[21] Appl. No.: 317,481

[22] Filed: Mar. 1, 1989

Related U.S. Application Data

[63] Continuation-in-part of Ser. No. 922,923, Oct. 24, 1986, Pat. No. 4,732,990, and a continuation-in-part of Ser. No. 91,010, Aug. 28, 1987, Pat. No. 4,883,655.

[51] Int. Cl.$^5$ .................. A61K 7/075; C07D 401/06; C07D 417/06; C07D 419/06
[52] U.S. Cl. .................. 424/70; 548/215; 548/237; 548/240; 548/261; 548/336; 548/364; 548/122; 548/123; 548/180; 548/187; 424/47; 424/71; 424/49; 540/467; 540/451; 540/524; 544/58.2; 544/58.5; 544/58.6; 544/60; 544/90; 544/98; 544/130; 544/141; 546/198; 546/199; 546/209; 546/210; 546/211
[58] Field of Search .............. 540/531, 451, 542, 467, 540/524; 546/243, 209, 198, 199, 210, 211; 548/550, 236, 336, 122, 123, 180, 187, 215, 237, 240, 261, 364; 544/141, 60, 58.2, 58.5, 58.6, 90, 98, 130; 424/70, 47, 71, 49

[56] References Cited

U.S. PATENT DOCUMENTS

| 2,945,863 | 7/1960 | Buc et al. | 260/326.3 |
| 3,138,610 | 6/1964 | Buc et al. | 260/309.6 |
| 3,914,403 | 10/1975 | Valan | 8/127.51 X |
| 4,534,877 | 8/1985 | Russell et al. | 424/70 X |

Primary Examiner—Joseph Paul Brust
Attorney, Agent, or Firm—Marilyn J. Maue; Joshua J. Ward

[57] ABSTRACT

The invention relates primarily to quaternized polycyclic compounds having the formula

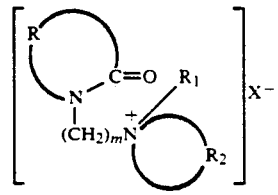

wherein m is an integer having a value of from 1 to 4; R is alkylene having from 3 to 8 carbon atoms and is optionally substituted with $C_1$ to $C_4$ alkyl; $R_2$ together with the quaternary nitrogen, forms a 5 to 14 membered heterocyclic ring, said ring containing at least 2 hetero atoms selected from the group of nitrogen, sulfur and oxygen; $R_1$ forms a double bond in the heterocyclic ring of the quaternized nitrogen or is alkyl, alkyleneoxyalkyl, alkylhydroxy, aryl, aralkyl, aralkenyl, alkaryl, alkylamidoalkyl and $X^-$ is an anion. The invention also relates to the preparation and use of said quaternized polycyclic compounds.

19 Claims, No Drawings

QUATERNIZED NITROGEN CONTAINING POLYCYCLIC COMPOUNDS

This application is a continuation-in-part of co-pending U.S. patent application Ser. No. 922,923, filed Oct. 24, 1986, now U.S. Pat. No. 4,732,990 and Ser. No. 091,010, filed Aug. 28, 1987, now U.S. Pat. No. 4,883,655 both entitled QUATERNIZED NITROGEN CONTAINING COMPOUNDS.

In one aspect the invention relates to novel quaternized polycyclic compounds which possess viscosity enhancing and hair conditioning properties, particularly in the presence of anionic surfactants. In another aspect the invention relates to novel quaternized polycyclic compounds having bactericidal properties. Still another aspect of the invention relates to the preparation of said quaternized polycyclic compounds and in still another aspect, the invention relates to the use of said compounds in several fields of application.

BACKGROUND OF THE INVENTION

The selection of components for hair and skin treating formulations presents numerous difficulties involving compatibility. Several hair treatment and shampoo formulations have been developed which aim to provide conditioning action during cleansing so as to leave the hair soft, manageable and lustrous and thus to eliminate a separate application of creme rinses or conditioning treatments. Problems arise from the limited compatibility of anionic detergents with commercial cationic conditioning agents which precipitate out of solution in shampoo formulations.

Shampoo formulations have employed conventional anionic surfactants such as sodium lauryl sulfate, ammonium lauryl sulfate, ammonium lauryl ether sulfate and sodium lauryl ether sulfates which have been found to be incompatible with most cationic conditioning at effective concentration levels.

Additionally, reproducible thickening formulations containing anionic detergents such as sodium α-olefin sulfonates is very difficult to achieve.

Still another problem encountered in hair conditioning shampoos is one of a preservative nature. It has been found that shampoos, containing inadequate preservative, on standing develop strands of Pseudomonas aerouginosa which are clearly visible in the liquid and which may cause scalp infection. Consequently, separate preservatives are added to the formulation to prevent development of this bacteria and prevent skin infection. These and many other problems are encountered in the formulation of various shampoos, conditioners and cream rinses. Certain of these difficulties are also encountered in skin lotions, healing salves, mouthwashes, etc.

Accordingly it is an object of this invention to minimize or obviate the above problems while providing additional benefits in hair and skin treating formulations.

Another object of the invention is to provide novel quaternized nitrogen containing compounds having unique properties.

Another object is to provide novel quaternized nitrogen containing compounds having excellent hair conditioning and thickening properties when incorporated into a shampoo and having high compatibility with components of hair and skin treating formulations.

Another object is to provide an economical and commercially feasible method for the preparation of said novel quaternized nitrogen containing compounds.

Still another object is to provide processes for the use of said quaternized compounds.

These and other objects will become apparent from the following description and disclosure.

THE INVENTION

According to this invention there is provided quaternized polycyclic compounds having unique properties and defined by the formula

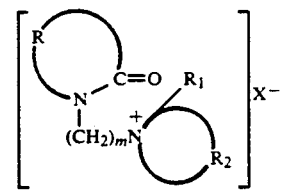

wherein $X^-$ is an anion; m is an integer having a value of from 1 to 4; R is linear alkylene having from 3 to 8 carbon atoms and is optionally substituted with $C_1$ to $C_4$ alkyl; $R_1$ forms a double bond in the heterocyclic ring with the quaternized nitrogen or is alkyl, alkyleneoxyalkyl, alkoxy, alkylhydroxy, aryl, aralkyl, aralkenyl, alkaryl and alkyleneamidoalkyl, said groups containing up to 30 carbon atoms; and $R_2$ together with the quaternary nitrogen atom forms a 5 to 10 membered monocyclic ring, a 9 to 10 membered bicyclic ring or a 13 to 14 membered tricyclic ring, at least one of said rings containing at least 2 hetero atoms selected from the group of sulfur, nitrogen and oxygen and being saturated or unsaturated as may occur for example in the rings of 1,4-thiazine, 1,4-oxazine, antipyrine, 1,2-oxazocine, oxazolidine, thiazolidine, oxathiazole, morpholine, isothia-diazine, benzodithiazole, benzoxathiazole or an oxide of thiazine. As indicated, a heterocyclic ring of the $R_2$ can be substituted with oxygen or an alkyl group. The quaternized heterocyclic moieties containing sulfur or oxygen heteroatoms exhibit antibacterial properties in addition to keratin conditioning properties.

Preferred compounds within the above group are those wherein m is 1; R is —$CH_2$—$CH_2$—$CH_2$—; $R_1$ is a double bond or a group having $C_8$ to $C_{22}$ carbon atoms, most preferably alkyl and $X^-$ is a halide or organic anion such as a tosylate, a sulfate or a sulfonate. The most preferred compounds of this group are those wherein $R_2$ together with the quaternized nitrogen forms a oxazolidinyl, thiazolidinyl, morpholinyl ring. Examples of the present polycyclic compounds include:

N-hexadecyl-N-[(2-pyrrolidonyl)methyl] 1,2-oxazocinium chloride

N-octadecyl-N-[(2-pyrrolidonyl)methyl] 1,4-oxazinium sulfate

N-ethyl-N-[(2-piperidonyl)methyl] 1,4-thiazinium methyl sulfonate

N-octadecyl-N-[(2-pyrrolidonyl)ethyl] antipyrinium tosylate

N-ethyl-N-[(2-piperidonyl)methyl] oxathiazolinium chloride

N-dodecyl-N-[(2-pyrrolidonyl)methyl] isothiazinium tosylate

N-heptadecyl-N-[(2-pyrrolidonyl)methyl] oxazocinium chloride

N-pentadecyl-N-[(2-pyrrolidonyl)methyl] benzoxathiazolinium methyl sulfonate
N-tridecyl-N-[(2-pyrrolidonyl)methyl] isothiazinium tosylate
N-octadecyl-N-[(2-pyrrolidonyl)methyl] thiazolidinium chloride
N-tetradecyl-N-[(2-pyrrolidonyl)methyl] oxazolidinium chloride
N-methyl-2-dodecyl-N-[(2-pyrrolidonyl)methyl] thiazinium tosylate
N-hexadecyl-N-[(2-pyrrolidonyl)methyl] 1,4-thiazinium tosylate
N-octadecyl-N-[(2-pyrrolidonyl)methyl] 1,4-oxazinium ethyl sulfonate
N-ethyl-N-[(2-pyrrolidonyl)methyl] morpholinium chloride
N-methyl-N-[(2-pyrrolidonyl)methyl] morpholinium tosylate
N-octadecyl-N-[(2-pyrrolidonyl)methyl] morpholinium methyl sulfate
N-octadecyl-N-[(2-azacycloheptanonyl)methyl] morpholinium ethyl sulfonate
N-ethyl-N-[(2-pyrrolidonyl)methyl] morpholinium chloride
N-methyl-N-[(2-pyrrolidonyl)methyl] morpholinium tosylate
N-ethyl-N-[(2-pyrrolidonyl)methyl] isothiazinium tosylate
N-methyl-N-[(2-pyrrolidonyl)methyl] benzthiazolinium methyl sulfate
N-ethyl-N-[(2-pyrrolidonyl)methyl] benzoxathiazolinium tosylate
N-octadecyl-N-[(2-pyrrolidonyl)methyl] 1,2-oxazinium methyl sulfonate
N-dodecyl-N-[(2-pyrrolidonyl)methyl] 1,2-oxazocinium ethyl sulfonate
N-hexyl-N-[(2-pyrrolidonyl)methyl] oxathiazolinium ethyl sulfate
N-ethyl-N-[3(2-pyrrolidonyl)propyl] morpholinium ethyl sulfate
N-methyl-N-[2(2-pyrrolidonyl)ethyl] morpholinium methyl sulfate
N-octadecyl-N-[(2-pyrrolidonyl)methyl] benzoxathiazolinium chloride
N-hexyl-N-[(2-pyrrolidonyl)methyl] oxathiazolinium tosylate It will be understood that the bromide and iodide salts of the above chlorides, sulfates, sulfonates or tosylates are also within the scope of this invention.

More specifically, the products of this group can be described by the formula:

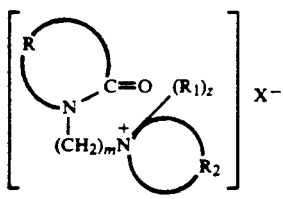

wherein z has a value of zero when the quaternized nitrogen atom is bonded in the heterocyclic ring by a double bond and a value of one when the quaternized nitrogen atom is bonded in the heterocyclic ring by two single bonds. All of the remaining definitions of R, $R_2$, $R_1$ and m being the same as set forth above.

The present quaternary compounds possess unique properties, among which is their ability to build viscosity, e.g. for liquids having a viscosity less than 50 centipoises, while simultaneously providing a hair and skin conditioning capability in cosmetic formulations which may or may not contain anionic surfactants. They are also useful in textile treating formulations to provide a softer, silky texture. For the purposes of this invention, the term "conditioning" is intended to include the functions of moisturizing, softening, cleansing, penetrating, luster enhancing, hair combability, dye leveling, dye retention and others. These compounds are highly compatible with α-olefin sulfonates and anionic surfactant salts conventionally employed in shampoos, skin lotions and like formulations. Their compatibility is such that up to 5% by weight or more of the quaternized compounds can be incorporated in a composition, a characteristic which permits the formation of effective formulations as liquids or gels. In contrast, most prior quaternary viscosity building conditioning compounds are incorporatable only up to 0.5 or 1 wt. percent based on total anionic content. The sulfur-containing compounds are outstanding for their biocidal properties and can be used in a mouthwash or as a highly compatable preservative in shampoo, hair conditioners, hand or body lotions and medicinal formulations. It is contemplated that mixtures of the oxygen or sulfur hetero pyrrolidonyl compounds can be employed in shampoos, hair conditioners and lotions as an agent which incorporates thickening, conditioning and preservative qualities in one additive; thus eliminating the need for separate chemical components to accomplish these individual needs. These mixtures and particularly the sulfur-containing quaternized products, may also be used to control dandruff or bacterial infections of the scalp and body skin. Generally, the quaternary compounds of this invention are mixed with a standard formulation of shampoo, cream rinse, hand or body lotion or creams, mouthwash, etc., in an effective amount which ranges from between about 0.05 to about 8% by weight, preferably between about 0.5 and about 5% by weight, of the total formulation. The compatability of the present compounds with anionic α-olefin sulfonates is surprising since most anionic compounds cause precipitation of cationic agents. However, the present compounds in concentrations up to 5% by weight show no tendency to precipitate after extended periods including periods up to 6 months or more.

The quaternary pyrrolidonyl compounds of this invention are prepared by an economically feasible process which involves the reaction between the corresponding heterocyclic amine and a N-haloalkyl lactam having a 5 to 10 membered ring. A general equation for the preparation of the present compounds is shown in the equation:

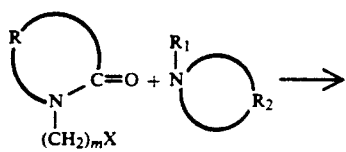

-continued

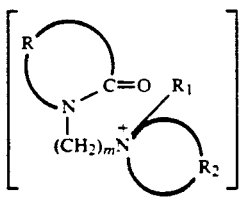

wherein m, R, $R_1$, $R_2$, $R_3$ and $X^-$ are as defined above and X an organic or halide anion.

Examples of suitable lactam reactants include the N-chloromethyl, N-bromomethyl and N-iodomethyl derivatives of 2-pyrrolidone, 4-methyl-2-pyrrolidone, 4-butyl-2-pyrrolidone, 2-piperidone, methyl-2-piperidone, 2-azacycloheptanone, 2-azacyclooctanone, 2-azacyclononanone, 2-azacyclodecanone and $C_1$ to $C_4$ alkyl derivatives substituted on an alkylene group in the heterocyclic ring of these lactams. Mixtures of these lactam reactants can also be employed to provide a correspondingly mixed quaternary product, if desired. Of these lactam reactants the N-halomethyl-2-pyrrolidones and N-halomethyl caprolactams are preferred and the N-chloromethyl lactams are most preferred.

Suitable nitrogen heterocyclic amino coreactants include any of the compounds defined by the aforementioned

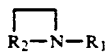

heterocyclic group. Preferred of this group are pyridine, oxazolidine and N-alkyl substituted pyrrolidines, piperidines, morpholines and imidazoles wherein most preferably the alkyl bonded to the heterocyclic nitrogen contains from 8 to 20 carbon atoms. Also, the most preferred heterocyclic amine coreactants of this invention are those wherein $R_2$ is a hydrocarbon group having a total of 4 or 5 carbon atoms.

The process is effected by reacting the haloalkyl lactam and the nitrogen heterocyclic amine coreactant at a temperature between about 25° and about 120° C., preferably between about 30° and about 60° C., under a pressure of from about 0 to about 50 psig, preferably atmospheric pressure, for a period up to about 10 hours, usually not more than 2 hours is required to complete the reaction. From the above equation, it is seen that stoichiometric amounts of haloalkyl lactam and amine are used in the reaction. However, an excess of one or the other of the components is practicible in the process. Generally, for economic considerations, and where the coreactant contains a single quaternizable site, a mole ratio of between 1:1.5 and about 1.5:1 is employed; although, a slight excess of the tertiary amino coreactant to insure complete reaction of the lactam is recommended. Accordingly, the most preferred mole ratio of lactam to amine is about 1:1.01–1:1.03.

It is to be understood, however, that in instances where more than one quaternizable site is present in the coreactant, the molar amount of the haloalkyl lactam can be increased accordingly.

The halide salt products obtained by the above process can be reacted with an ion exchange resin, such as a tosylate, a sulfate or a sulfonate, to provide the corresponding quaternized salt product if desired. Alternatively, the tosylate, sulfate or sulfonate quaternized salt can be produced directly by reacting the corresponding lactam salt with the tertiary amine under the aforedescribed conditions.

It is recommended that the haloalkyl lactam be added gradually or dropwise to the amine at the beginning of the ensuing exothermic reaction. At the completion of the reaction, a solid product is formed and recovered. Since the reaction is quantitative, the product can be used as is or, when a slight excess of the amine is employed, it can be neutralized with a weak acid such as acetic, lactic or citric acid.

For incorporating into a standard formulation of shampoo, cream rinse, hand or body lotion, etc., the present product is dissolved in an inert solvent such as water, propylene glycol, ethanol, etc., and the solution in the desired amount is mixed into the formulation to provide a homogeneous liquid, gel, cream or lotion. Incorporation of the present product is usually affected at room temperature under atmospheric pressure and requires no special formulating technique. However, for certain formulations incorporation of the present product can be effected at temperatures up to about 85° C. Amphoteric- containing shampoo formulations are best prepared by initially preparing an aqueous solution of the quaternized product and the amphoteric surfactant and then adding the solution to the shampoo formulation.

Having generally described the invention, reference is now had to the accompanying examples which set forth preferred embodiments, but which are not to be construed as limiting to the scope of the invention as more broadly set forth above and in the appended claims.

EXAMPLE I

To a 1 liter, 4-neck flask equipped with mechanical stirrer, reflux condenser, thermometer, and dropping funnel is added N-octadecyl thiazolidine which is heated with stirring to 70° C. under $N_2$ blanket after which the heating source is removed and N-chloromethyl-2-pyrrolidone (0.5 mole) is added to the amine dropwise over a period of 25 minutes. The exothermic reaction which ensues is controlled at 100° C. by the rate of addition of N-chloromethyl-2-pyrrolidone. The reaction mixture is changed from a liquid to a paste during the addition of N-chloromethyl-2-pyrrolidone and finally to a solid (powder) on completion of the reaction. The yield of N-octadecyl-N-[(2-pyrrolidonyl)methyl] thiazolidinium chloride, m.p. 160°–162° C., is quantitative.

EXAMPLE II

The reaction of Example I is repeated except that the amine used is N-ethyl-morpholine (2% molar excess with respect to N-chloromethyl-2-pyrrolidone). The product, N-ethyl-N-[(2-pyrrolidonyl)methyl] morpholinium chloride is recovered as a paste in quantitative yield.

EXAMPLE III

The process of Example I is repeated except that the amine used is N-octadecyl oxazolidine. The yield of N-octadecyl-N-[(2-pyrrolidonyl)methyl] oxazolidinium chloride is quantitative.

EXAMPLE IV

The process of Example I is repeated except that the amine used is N-hexadecyl-5-methyl-isoxazolidine. The yield of N-hexadecyl-5-methylN-[(2-pyrrolidonyl)methyl] isooxazolidinium chloride is essentially quantitative.

EXAMPLE V

The process of Example I was repeated except that the amine used is N-hexadecyl 1,2-oxazolin. The yield of N-hexadecyl-N-[(2-pyrrolidonyl)methyl] 1,2-oxazolinium chloride is quantitative.

EXAMPLE VI

The process of Example I was repeated except that the amine used is N-ethyl oxathiazolin. The yield of N-ethyl-N-[(2-pyrrolidonyl)methyl] oxathiazolinium chloride is quantitative.

EXAMPLE VII

The process of Example I is repeated except that the amine used was N-hexadecyl-isothiazine. The yield of N-hexadecyl-N-[(2-pyrrolidonyl)methyl] isothiazinium chloride is quantitative.

EXAMPLE VIII

The process of Example I was repeated except that the amine used is N-octadecyl-oxazolidine. The yield of N-octadecyl-N-[(2-pyrrolidonyl)methyl] oxazolidinium chloride is quantitative.

EXAMPLE IX

The process of Example I is repeated except that the amine used is N-octadecyl-morpholine. The yield of N-octadecyl-N-[(2-pyrrolidonyl)methyl] morpholinium chloride is quantitative.

EXAMPLE X

The process of Example I is repeated except that N-chloromethyl caprolactam is used instead of N-chloromethyl-2-pyrrolidone. The yield of N-octadecyl-N-[(2-azacycloheptanonyl)methyl] morpholinium chloride is quantitative.

EXAMPLE XI

Preparation of Tosylate Salt

To a glass chromatography column was charged 450 g. Amberlyte IRA 900 ion exchange resin*. The column was washed with one liter of methanol followed by one liter of distilled water.

* a macroreticular strongly anion exchange resin having a halide attached to the resin matrix of styrene/divinylbenzene A solution of sodium tosylate, prepared by addition of 332.9 g. p-toluenesulfonic acid monohydrate to 1720 g. water followed by neutralization with 140 g. of 50% sodium hydroxide, was then passed through the packed column at a rate sufficient to permit displacement of the Amberlyte halide and to replace it with toluene sulfonate. The column was then washed with one 1 liter of methanol. A solution of 153 g. of the product of Example X (98.4% pure) in 500 ml methanol was passed through the column at a rate sufficient to exchange the chloride anion with the toluene sulfonate of the resin. The column was then washed with 500 ml methanol and the methanol evaporated leaving 200 g. of 98% pure quaternized tosylate product. The product showed no loss of quaternary activity after storage at 50° C. for 60 days.

EXAMPLE XII

Example XI was repeated except that sodium methyl sulfonate was substituted for sodium toluene sulfonate and a solution of the product of Example IX was substituted for that of Example X. The resulting quaternized ammonium methylsulfonate product (94.3% pure quaternized compound) was recovered. This product showed high activity after being stored at 50° C. for 60 days.

EXAMPLE XIII

Example XI was repeated except that sodium ethyl sulfate was substituted for sodium toluene sulfonate and a solution of the product of Example IV was substituted for that of Example X. The resulting quaternized ammonium sulfate product (96.7% pure quaternized compound) was recovered and retained high activity after being stored at 50° C. for 60 days.

It is to be understood that any of the other quaternized halide salts disclosed herein can be converted to alkyl sulfate, sulfonate or tosylate salts by the methods described above in Examples XI, XII and XIII.

EXAMPLE XIV

Although all of the present quaternized compounds possess excellent surfactant properties, certain members are particularly recommended for incorporation into specific types of cosmetic formulations. Table I lists some of such uses for individual quaternized products within the scope of this invention, together with a brief description of the benefits derived from their incorporation.

Generally, the present products are added to the formulations in amounts between about 0.1 and about 5 wt. %, based on active ingredients. The quaternized compounds in Table I have the general formula:

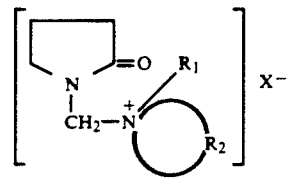

TABLE I

| COMPOUND NO. | $R_2/R_1/X$ | Suitable for Formulation in | Benefit Realized |
|---|---|---|---|
| 1. | $-(CH_2)_3-S-(CH_2)_3-/-C_2H_5/Cl$ | cream rinse | improved wet/dry combing-luster-softness |
| 2. | $-(CH_2)_2-O-(CH_2)_2-/-C_6H_4-C_8H_{17}/Cl$ | cream rinse & hair conditioner | same as above + overall conditioning |

TABLE I-continued

| COMPOUND NO. | $R_2/R_1/X$ | Suitable for Formulation in | Benefit Realized |
|---|---|---|---|
| 3. | (N-methyl pyrrolidinone ring)=O/—$C_6H_5$/Cl | moisturizing lotion | high compatability in formulation-good skin substantivity and penetration. |
| 4. | (thiane ring)/—$CH_3$/tosylate | cream hair rinse | softness-combability-shine |
| 5. | (pyran ring)/—$C_{18}H_{37}$/$CH_3$sulfonate | syndet bar & after sun lotion | improved moisturizing-good penetration |
| 6. | (pyridine ring)/—$C_{14}H_{29}$/Cl | fabric softener | improved softness of hand |
| 7. | (N-ethyl benzimidazole ring)/*/Br | hair & skin medicant | anti-dandruff properties-skin cleansing |
| 8. | (benzofuran-type ring)/—$C_{16}H_{33}$/$C_2H_5$sulfate | moisturizing lotion | high compatability with formulating agents-good skin substantivity and penetration |
| 9. | (benzothiophene ring)—$CH_3$/—$C_{12}H_{25}$/Cl | conditioning shampoos | overall conditioning & cleansing-compatability with anionic agents |
| 10. | —CH=CH—O—CH=CH—/—$C_{12}H_{25}$/tosylate | hot oil hair treating lotion | improved conditioning-luster & shine-imparts body |
| 11. | (thiane ring)/—$C_{16}H_{33}$/Cl | oily hair shampoo | greasless conditioning-body building-improved wet/dry combability |
| 12. | (benzothiazole ring) S/—$C_6H_4$—$CH_3$/Cl | dandruff shampoo & skin medicant | improved cleansing and disinfectant |
| 13. | (sulfoxide ring, S=O)/—$C_{12}H_{24}$/Cl | dandruff shampoo & skin medicant | good antibacterial and fungicidal properties |
| 14. | (sulfone ring, O=S=O)/—$C_{16}H_{33}$/Cl | dandruff shampoo & skin medicant | good antibacterial & fungicidal properties |

*forms a double bond with the quaternized nitrogen

EXAMPLE XV

Examples of specific formulations for the above uses achieving the benefits noted are presented as follows.

| Ingredients | Parts by Weight |
|---|---|
| CREAM RINSE | |
| Compound No. 1 in Table I | 2.0 |
| cetyl alcohol | 2.0 |
| emulsifying wax | 2.0 |

-continued

| Ingredients | Parts by Weight |
|---|---|
| citric acid | to pH 4 |
| deionized water | qs |
| fragrance | qs |
| preservative | qs |
| HAIR CONDITIONER | |
| Compound No. 2 in Table I | 4.0 |
| PEG-8 Distearate | 2.5 |
| mineral oil | 1.5 |
| lanolin alcohol | 1.0 |
| stearic acid | 1.0 |
| PPG-20 methyl glucose ether | 1.0 |
| hydrolized animal protein | 0.25 |
| citric acid | to pH 4 |
| deionized water | qs |
| preservative | qs |
| fragrance | qs |
| BLOW DRY STYLING LOTION | |
| Compound No. 3 in Table I | 1.5 |
| ethanol | 3.0 |
| polyquaternium* 11 | 2.0 |
| PEG-10 Castor oil | 0.2 |
| fragrance | 0.2 |
| phosphoric acid | to pH 6 |
| deionized water | qs |
| CONDITIONING HAIR SPRAY | |
| Compound No. 9 in Table I | 0.6 |
| ethanol | 75.0 |
| ethyl ester of PVM/MA** copolymer | 4.1 |
| 2-amino-2-methyl-1-propanol 99% | 0.1 |
| fragrance | 0.2 |
| propellant | 20.0 |

*the quaternized ammonium polymer formed by reacting dimethyl sulfate and a copolymer of vinyl pyrrolidone and dimethylamino methylacrylate
**vinyl methyl ether/maleic anhydride

| CONDITIONING SHAMPOO | |
|---|---|
| Compound 10 in Table I | 3.0 |
| N-dodecyl-2-pyrrolidone | 0.6 |
| polyquaternium 11 | 0.5 |
| sodium laureth-4-phosphate | 0.8 |
| ammonium lauryl sulfate | 40.0 |
| silk protein | 0.25 |
| tetrasodium ethylenediamine tetra-acetic acid | 0.2 |
| deionized water | qs |
| colorant | qs |
| fragrance | qs |
| MOISTURIZING LOTION | |
| Compound No. 8 in Table I | 2.0 |
| mineral oil 70 CTS | 2.0 |
| stearic acid | 3.0 |
| emulsifying wax | 3.0 |
| Dimethicone* 200 CTS | 1.5 |
| Carbomer 934** | 0.15 |
| Oleth-20*** | 1.0 |
| triethanolamine 98% | 1.0 |
| deionized water | qs |
| preservative | qs |
| fragrance | qs |

*a mixture of methylated siloxane polymers end-blocked with trimethyl siloxy units (dimethylpolysiloxane)
**cross-linked polymer of acrylic acid
***PEG ether of oleyl alcohol

| BUBBLE BATH | |
|---|---|
| Compound No. 5 in Table I | 3.0 |
| ammonium nonoynol-4-sulfate | 30.0 |
| sodium cocoyl isothionate | 10.0 |
| cocamidopropyl hydroxysultaine | 10.0 |
| cocamide diethanolamide | 6.0 |
| sodium methyl cocoyl taurate | 20.0 |
| aloe vera gel | 1.0 |
| coconut oil | 1.0 |
| glycol stearate | 1.0 |
| deionized water | qs |
| preservative | qs |
| colorant | qs |
| SHAMPOO FOR OILY HAIR | |
| Compound No. 11 in Table I | 3.0 |
| N-dodecyl-2-pyrrolidone | 1.0 |
| tetrasodium ethylenediamine tetra-acetic acid | 0.2 |

-continued

| Ingredients | Parts by Weight |
|---|---|
| sodium lauryl sulfate | 20.0 |
| alpha-olefin sulfonate | 20.0 |
| polyquaternium 11 | 0.5 |
| deionized water | qs |
| preservative | qs |
| colorant | qs |
| fragrance | qs |
| added inorganic salts as desired for viscosity modification | |
| MOUTHWASH | |
| Compound No. 6 in Table I | 0.05 |
| alcohol, 190° | 20.00 |
| thymol | 0.03 |
| glycerine | 10.00 |
| flavor | 2.0 |
| distilled water | qs |
| polysorbate 80 | 2.00 |
| SYNDET BAR (Superfatted) | |
| Compound No. 5 in Table I | 0.5 |
| stearic acid, triple pressed | 32.00 |
| kettle soap | 9.80 |
| sodium cocoyl isethionate | 49.00 |
| sodium methyl cocoyl taurate | 6.90 |
| citric acid, 50% aqueous | 0.60 |
| titanium dioxide | 0.20 |
| fragrance | 1.00 |
| WATER RESISTANT EMOLLIENT AFTER SUN LOTION | |
| Compound No. 8 in Table I | 3.0 |
| mink Oil, Light Fraction | 11.00 |
| glyceryl stearate, self emulsifying | 1.00 |
| stearic acid | 2.50 |
| mineral oil and lanolin alcohol | 2.00 |
| myristyl myristate | 3.000 |
| mineral oil | 10.00 |
| PVP/Eicosene copolymer | 2.00 |
| triethanolamine | 0.70 |
| sorbitol | 3.00 |
| hydroxyethylcellulose | 0.30 |
| distilled water | qs |
| preservative | qs |
| fragrance | qs |
| NON-ALCOHOLIC CONDITIONING MOUSSE | |
| Compound No. 6 in Table I | 5.00 |
| PVP K-30 | 2.00 |
| Oleth-20 | 0.50 |
| fragrance | qs |
| deionized water | 77.50 |
| propellant A-46 | 15.00 |
| SELF-HEATING AEROSOL SHAVING CREAM | |

Employed dual dispensing valve for metering oxidant from $H_2O_2$ container and reductant from aerosol can.

| Compound No. 12 in Table I | 2.00 |
|---|---|
| stripped coconut fatty acid | 1.10 |
| sorbitol | 10.00 |
| stearic acid | 4.20 |
| PEG-40 soritan peroleate | 2.00 |
| triethanolamine | 3.00 |
| potassium hydroxide | 1.00 |
| potassium sulfite | 9.00 |
| fragrance | 0.80 |
| butyrated hydroxy toluene (BHT) | 0.01 |
| butyrated hydroxy anisole (BHA) | 0.01 |
| deionized water | qs |
| propellant | qs |
| HAIR MIST CONDITIONER (w/o added preservative) | |
| 50/50 Mixture No. 2 & 6 in Table I | 1.00 |
| propylene glycol dicaprylate/ dicaprate copolymer | 0.30 |
| oleamidopropyl dimethylamine | 0.50 |
| deionized water | 98.2 |
| CATIONIC MOUSSE HAND/BODY LOTION | |

(Used 85 Parts of the following formula to 15 parts propellant A-46)

| Compound No. 8 in Table I | 0.50 |
|---|---|
| acetylated polyoxyethylene lanolin | 2.00 |
| ethoxylated lanolin alcohols | 1.00 |

| Ingredients | Parts by Weight |
|---|---|
| glyceryl stearate, self-emulsifying | 5.50 |
| cetyl alcohol | 1.50 |
| mineral oil, 70 CTS | 1.50 |
| stearyl alcohol | 1.50 |
| glycerin | 3.00 |
| isopropyl myristate | 4.00 |
| dimethicone, 100 CTS | 2.00 |
| water | qs |
| preservative | qs |
| fragrance | qs |
| HOT OIL TREATMENT - (w/o added preservative) | |
| 50/50 mixture No. 10 & 11 in Table I | 1.50 |
| oleamidopropyl dimethyl amine | 1.00 |
| polyethylene glycol 6000 distearate | 2.00 |
| hexylene glycol | 4.00 |
| lactic acid, 88% | to pH 4.4 |
| color | qs |
| deionized water | qs |
| AFTER SHAVE BALM | |
| 50/50 mixture No. 9 & 11 in Table I | 1.00 |
| Carbomer 941 | 0.20 |
| tetrasodium ethylene diamine tetra-acetic acid | 0.10 |
| cetearyl alcohol* and polyethylene glycol ether of cetearyl alcohol | 2.50 |
| isopropyl myristate | 1.00 |
| Oleth-20 | 1.00 |
| methyl gluceth 20 | 2.00 |
| triethanolamine, 98% | 0.20 |
| propylene glycol | 3.00 |
| SDA denatured alcohol | 7.50 |
| PVP/dimethylaminoethyl methacrylate | 7.00 |
| fragrance | 1.00 |
| distilled water | qs |
| DANDRUFF SHAMPOO AND SKIN MEDICANT | |
| Compound No. 7 or 12 in Table I | 4.2% |
| Sodium lauryl sarcosinate, 30% | 10.0 |
| TEA lauroyl sulfate, 40% | 25.0 |
| Magnesium aluminium silicate | 1.0 |
| Hydroxymethyl cellulose, E 4000 | 1.25 |
| Water, perfume, color (D & C Green #5) | qs |

*50/50 mixture of cetyl and stearyl alcohols

The above examples are representative of preferred embodiments of the present invention; however, it will be understood that other species of instant quaternized lactams can be substituted in the above formulations to provide the benefits indicated. Also, in the preparation of the quaternized lactams described in Examples I-XIII, other lactams and/or cyclic tertiary amino compounds described herein can be substituted to provide the corresponding quaternized products within the scope of this invention Particularly recommended among these substituted species are the halomethyl-2-caprolactam reactants and the amidoalkyl-substituted or hydroxy-substituted heterocyclic amine reactants having from 3 to 8 carbon atoms which also provide useful bactericidal and viscosity enhancing properties.

What is claimed is:

1. A quaternized polycyclic compound having the formula:

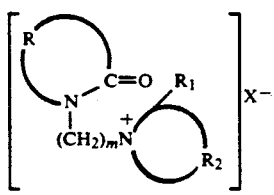

wherein $X^-$ is an anion; m is an integer having a value of from 1 to 4; R is linear alkylene having from 3 to 8 carbon atoms and is optionally substituted with $C_1$ to $C_4$ alkyl; $R_1$ forms a double bond in the heterocyclic ring with the quaternized nitrogen or is alkyl, alkyleneoxyalkyl, alkoxy, alkylhydroxy, aryl, aralkyl, aralkenyl, alkaryl or alkyleneamidoalkyl, said groups containing up to 30 carbon atoms; and $R_2$ together with the quaternary nitrogen atom forms a heterocyclic ring selected from the group consisting of

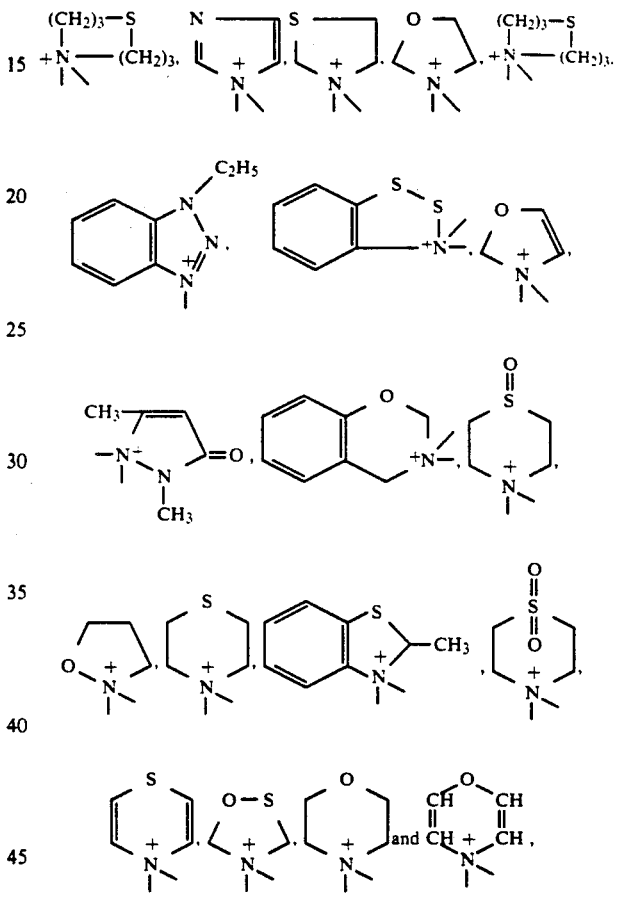

said heterocyclic rings being optionally substituted with alkyl.

2. The compound of claim 1 wherein R is alkylene having up to 4 carbon atoms and is optionally substituted with lower alkyl.

3. The compound of claim 1 wherein $R_1$ is an organic radical having from 6 to 22 carbon atoms.

4. The compound of claim 1 wherein $R_1$ forms a double bond with the quaternary nitrogen atom.

5. The compound of claim 1 wherein said quaternized heterocyclic ring contains in addition to the quaternized nitrogen atom, a heteroatom selected from the group of oxygen and sulfur.

6. The compound of claim 1 wherein $R_2$ together with the quaternized nitrogen atom forms a oxathiazolinium heterocyclic ring.

7. The compound of claim 1 wherein $R_2$ together with the quaternized nitrogen atom forms a morpholinyl ring.

8. The compound of claim 1 wherein $R_2$ together with the quaternized nitrogen atom forms a imidazole ring.

9. The compound of claim 1 wherein $R_2$ together with the quaternized nitrogen atom forms a oxazolidinyl ring.

10. The compound of claim 1 wherein $R_2$ together with the quaternized nitrogen atom forms a benzodithiazole ring.

11. The compound of claim 1 wherein $R_2$ together with the quaternized nitrogen atom forms a thiazolidinyl ring.

12. The composition comprising a cosmetic formulation and an effective conditioning amount of the compound of claim 1.

13. The composition of claim 12 wherein said cosmetic formulation is a hair or skin treating formulation.

14. The composition of claim 12 wherein said formulation is a shampoo and $R_2$ in the compound contains a sulfur or oxygen heteroatom.

15. The composition of claim 12 wherein said formulation contains between about 0.05 and about 8 weight % of said compound.

16. The composition of claim 15 wherein said formulation contains between about 0.5 and about 5 weight % of said compound.

17. The composition of claim 15 wherein the formulation additionally contains up to 5 weight % of an anionic surfactant.

18. The process of applying an effective conditioning amount of the compound of claim 1 to hair or skin.

19. The process of adding an effective preservative amount of the compound of claim 1 to a shampoo formulation.

* * * * *